United States Patent [19]

Marhold et al.

[11] Patent Number: 5,041,683

[45] Date of Patent: Aug. 20, 1991

[54] NUCLEAR-FLUORINATED TRIFLUOROMETHYLBENZALDEHYDES

[75] Inventors: Albrecht Marhold, Leverkusen; Rudolf Braden, Odenthal, both of Fed. Rep. of Germany

[73] Assignee: Bayer Aktiengesellschaft, Leverkusen, Fed. Rep. of Germany

[21] Appl. No.: 514,387

[22] Filed: Apr. 25, 1990

[30] Foreign Application Priority Data

May 12, 1989 [DE] Fed. Rep. of Germany ....... 3915495

[51] Int. Cl.$^5$ .............................................. C07C 47/55
[52] U.S. Cl. ..................... 568/425; 568/437
[58] Field of Search ................................ 568/425, 437

[56] References Cited

FOREIGN PATENT DOCUMENTS 0145334 6/1985 European Pat. Off. ........... 568/425

*Primary Examiner*—Werren B. Lone
*Attorney, Agent, or Firm*—Sprung Horn Kramer & Woods

[57] ABSTRACT

Process for the preparation of nuclear-fluorinated trifluoromethylbenzaldehydes from nuclear-chlorinated trifluoromethylbenzaldehydes, and new nuclear-fluorinated trifluoromethylbenzaldehydes.

1 Claim, No Drawings

NUCLEAR-FLUORINATED TRIFLUOROMETHYLBENZALDEHYDES

The present invention relates to a process for the preparation of nuclear-fluorinated trifluoromethyl-benzaldehydes which can, if appropriate, additionally be chlorinated in the nucleus, and to new nuclear-fluorinated trifluoromethylbenzaldehydes which, if appropriate, are also chlorinated in the nucleus.

It is known to convert nuclear-chlorinated benzaldehydes containing no $CF_3$ groups into the corresponding nuclear-fluorinated benzaldehydes by means of potassium fluoride (see Chemistry Letters 1988, pages 1355–1358). It can be seen from Table 1 therein that yields of approximately 70% can only be achieved in the presence of tetraphenylphosphonium salts and certain ethers (for example 18-crown-6), while tetraphenylphosphonium salts on their own, ethers on their own and the combination of a tetraalkylphosphonium salt with an ether give very poor yields (between only 43 and 5%). In a sensitive system of this type it cannot be foreseen how an additional $CF_3$ group, which greatly alters the distribution of electrons on the aromatic nucleus, will affect the possibilities of chlorine-3-fluorine replacement reactions.

It is known from European Offenlegungsschrift (European Published Application) 125,803 (see Example T) to prepare 2-chloro-3-trifluoromethyl-5-fluorobenzaldehyde and 2-trifluoromethyl-3-chloro-6-fluorobenzaldehyde by introducing a CHO group into 1-chloro-2-trifluoromethyl-4-fluorobenzene using butyllithium. The handling of butyllithium requires special technical effort. In addition, the yields which can be achieved are low. This procedure is therefore not very suitable for application on an industrial scale.

A process analogous to that of European Offenlegungsschrift (European Published Application) 125,803 for the preparation of 2-trifluoromethyl-3,6-difluorobenzaldehyde, 2,5-difluoro-3-trifluoromethylbenzaldehyde and 2-trifluoromethyl-3,5-dichloro-6-fluorobenzaldehyde is known from European Offenlegungsschrift (European Published Application) 174,131 (see Examples C and H).

A process has now been found for the preparation of nuclear-fluorinated trifluoromethylbenzaldehydes of the formula (I)

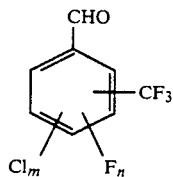

in which
n represents 1, 2 or 3 and
m represents 0, 1 or 2,
n + m being not more than 3,
which is characterized in that a nuclear-chlorinated trifluoromethylbenzaldehyde of the formula (II)

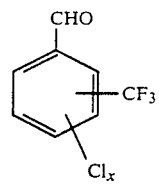

in which
x represents 1, 2 or 3,
is reacted with potassium fluoride at an elevated temperature in the presence of a solvent and in the absence of water.

Nuclear-chlorinated trifluoromethylbenzaldehydes of the formula (II), for example 4-chloro-3-trifluoromethylbenzaldehyde, 2,3-dichloro-4-trifluoromethylbenzaldehyde, 4,5-dichloro-2-trifluoromethylbenzaldehyde, 2,6-dichloro-3-trifluoromethylbenzaldehyde, 2,4-dichloro-5-trifluoromethylbenzaldehyde, 2,6-dichloro-4-trifluoromethylbenzaldehyde, 2,5-dichloro-4-trifluoromethylbenzaldehyde, 2-chloro-5-trifluoromethylbenzaldehyde, 4-chloro-2-trifluoromethylbenzaldehyde, 2-chloro-3-trifluoromethylbenzaldehyde, 2-chloro-4-trifluoromethyl 2,4,6-trichloro-3-trifluoromethylbenzaldehyde, 2,3,6-trichloro-4-trifluoromethylbenzaldehyde, 2,3,5-trichloro-4-trifluoromethylbenzaldehyie, 2,3,4-trichloro-6-trifluoromethylbenzaldehyde and 2,3,4-trichloro-5-trifluoromethylbenzaldehyde, which can be employed in the process according to the invention are for the most part known compounds which can be obtained, for example, as in Houben-Weyl, Methoden der org. Chemie ("Methods of Organic Chemistry"), volume E 3, pages 350 et seq. (1983). Insofar as formula (II) represents new compounds, these are accessible in a manner analogous to that for the known compounds.

The potassium fluoride can be employed, for example, in a ratio of 1 to 2 moles per mole of chlorine to be replaced by fluorine. This ratio is preferably 1.4 to 1.6 moles per mole of chlorine to be replaced.

The process according to the invention can be carried out, for example, at temperatures within the range of 160° to 210° C. It is preferable to carry out the reaction at 180° to 200° C. In general, the reaction is carried out under normal pressure. Carrying out the reaction under pressure or in a closed vessel can become necessary if the compound of the formula (II), the reaction products of the formula (I) and/or the solvent employed are volatile at the desired reaction temperature.

Suitable solvents are, in particular, polar, aprotic solvents, for example tetramethylene sulphone, N-methylpyrrolidone, dimethylacetamide, dimethylformamide, N-methylcaprolactam and dimethyl sulphoxide.

An adequate absence of water can be obtained, for example, by using anhydrous solvents and anhydrous starting materials of the formula (II). Potassium fluoride often contains small amounts of water. This can be removed, for example, by first introducing only potassium fluoride and solvent into the reaction vessel and distilling off the water together with a certain amount of solvent. Water present can also be removed by adding an aromatic compound, for example toluene or xylene, and distilling off the water as an azeotrope with the aromatic compound.

The process according to the invention can be carried out in the presence or absence of catalysts. Examples of suitable catalysts are quaternary salts, such as ammonium or phosphonium salts, if appropriate together with added salts of transition metals and/or crown ethers. Catalysts can be employed in amounts of, for example, 0.2 to 5% by weight, relative to the nuclear-chlorinated trifluoromethylbenzaldehyde of the formula (II) which is employed. It is also possible to use caesium salts, preferably halides, as additional catalysts. For economic reasons, the amounts of these are, for example, 0.2–10%, but can also be greater.

The product or products prepared can be isolated from the reaction mixture present after the reaction, and purified, by, for example, distillation. In this regard it is also possible to use vacuum distillation or steam distillation.

If the nuclear-chlorinated trifluoromethylbenzaldehyde employed contains several chlorine atoms (formula (II), x=2 or 3), one or more chlorine atoms or all the chlorine atoms can be replaced by fluorine. A selective chlorine/fluorine replacement is possible especially in the case of chlorine atoms which are present in the o-position or p-position relative to the CHO group. Chlorine atoms present in the m-position relative to the CHO group then remain unreplaced on the benzene nucleus at an appropriate dosage of potassium fluoride and if the reaction conditions used are not excessively severe. Thus, for example, it is possible to prepare 4-fluoro-5-chloro-2-trifluoromethylbenzaldehyde in good yields from 4,5-dichloro-2-trifluoromethylbenzaldehyde. In general, all the chlorine atoms present on the benzene nucleus can be replaced by fluorine if the dosage of potassium fluoride is appropriate and if relatively severe reaction conditions are used.

New nuclear-fluorinated trifluoromethylbenzaldehydes of the formula (Ia)

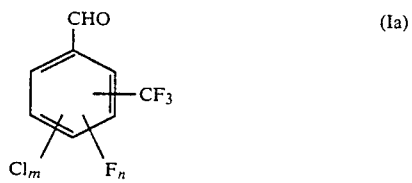

have also been found in which
n represents 1, 2 or 3 and
m represents 0, 1 or 2,
n+m being 2 or 3, and
the nuclear-fluorinated trifluoromethylbenzaldehydes prepared in accordance with EP-A 125,803 and EP-A 174,131 being excepted.

The following are preferred compounds of the formula (Ia):
2-trifluoromethyl-4,6-difluorobenzaldehyde,
2-trifluoromethyl-4-chloro-6-fluorobenzaldehyde,
2-trifluoromethyl-4-fluoro-6-chlorobenzaldehyie,
2-trifluoromethyl-4-fluoro-5-chlorobenzaldehyie,
2-trifluoromethyl-4,5-difluorobenzaldehyde,
2-trifluoromethyl-4,5-difluorobenzaldehyde,
3-trifluoromethyl-4-fluoro-5-chlorobenzaldehyde,
2,4-difluoro-3-trifluoromethylbenzaldehyde,
3-trifluoromethyl-4,6-difluorobenzaldehyde,
2-fluoro-4-trifluoromethyl-5-chlorobenzaldehyie,
2-fluoro-3-chloro-4-trifluoromethylbenzaldehyie,
2,4-difluoro-4-trifluoromethylbenzaldehyde,
2,6-difluoro-4-trifluoromethylbenzaldehyde,
2-chloro-4-trifluoromethyl-6-fluorobenzaldehyde,
3-chloro-4-trifluoromethyl-6-fluorobenzaldehyde,
2,6-difluoro-4-trifluoromethyl-5-chlorobenzaldehyde,
2,5,6-trifluoro-3-trifluoromethylbenzaldehyde,
2,6-difluoro-3-trifluoromethyl-5-chlorobenzaldehyde,
2,4,6-trifluoro-3-trifluoromethylbenzaldehyde,
2-trifluoromethyl-3-chloro-4,6-difluorobenzaldehyde and The compounds of the formula (Ia) can be obtained as described earlier in the text.

Nuclear-fluorinated trifluoromethylbenzaldehydes of the formula (I) are important intermediate products for the preparation of pharmaceutically active dihydropyridines. Dihydropyridines of this type can, for example, be prepared in accordance with European Offenlegungsschrift (European Published Application) 125,803 and European Offenlegungsschrift (European Published Application) 174,131 or in a manner analogous thereto. The new nuclear-fluorinated trifluoromethylbenzaldehydes of the formula (Ia) which are accessible in accordance with the invention widen the scope of the dihydropyridines accessible in this manner.

In the state of the art described initially it is decidedly surprising that it is possible in accordance with the invention to prepare known and new nuclear-fluorinated trifluoromethylbenzaldehydes in a simple manner which can readily be implemented on an industrial scale.

EXAMPLES

EXAMPLE 1

50 g of potassium fluoride were suspended in 120 ml of tetramethylene sulphone and were incipiently distilled at 15 mbar to achieve complete drying. 60 g of 4-chloro-3-trifluoromethylbenzaldehyde were then added and the mixture was heated at 190° C. for 7 hours with the exclusion of moisture. In the course of the reaction the temperature fell to 180° C. and boiling under reflux set in at the same time. After this, a conversion of more than 96% was indicated by gas chromatography. The reaction mixture thus obtained was subjected to steam distillation and was redistilled after the product had been separated off from the distillate. 45 g of 4-fluoro-3-trifluoromethylbenzaldehyde having a boiling point of 70° to 72° C. at 12 mbar were obtained.

EXAMPLE 2

Analogously to Example 1, 92 g of potassium fluoride in 290 ml of tetramethylene sulphone together with 116 g of 2,3-dichloro-4-trifluoromethylbenzaldehyde were heated for 7 hours in the presence of 5 g of tributylbenzylphosphonium chloride. After this, 16 g of 2,3-difluoro-4-trifluoromethylbenzaldehyde (boiling point 62 to 64° C. at 20 mbar, refractive index $n°_D$:1.4535) and 66 g of 2-fluoro-3-chloro-4-trifluoromethylbenzaldehyde (boiling point 88 to 90° C. at 20 mbar, refractive index $n_D^{20}$:1.4875) were obtained.

EXAMPLE 3

A mixture of 106 g of anhydrous potassium fluoride in 190 ml of tetramethylene sulphone (incipiently distilled at 15 mbar to achieve dryness), 6.6 g of tributylbenzylphosphonium chloride, 2.6 g of iron (III) chloride and 132 g of 4,5-dichloro-2-trifluoromethylbenzaldehyde was reacted for 7 hours at 190° C. After the mixture had been cooled, the reaction mixture was subjected to crude distillation at 15 mbar. Precision distillation of the distillate gave the following:

26 g of 4,5-difluoro-2-trifluoromethylbenzaldehyde having a boiling point of 42° to 45° C. at 12 bar and a refractive index $n^{20}_D$ of 1.4375 and 57 g of 5-chloro-4-fluoro-2-trifluoromethylbenzaldehyde having a boiling point of 69 to 70° C. at 12 mbar and a refractive index $n^{20}_D$ of 1.4745.

EXAMPLE 4

Example 3 was repeated, but heating was carried out for 5 hours at a temperature of 200° C. 42 g of the difluoro compound and 41 g of the fluorochloro compound were obtained.

EXAMPLE 5

Analogously to Example 1, 40 g of potassium fluoride were initially taken in 150 ml of tetramethylene sulphone and the mixture was incipiently distilled in vacuo, and then heated together with 3 g of tributylbenzylphosphonium chloride, 1 g of iron (III) chloride and 50 g of 2,5-dichloro-3-trifluoromethylbenzaldehyde for 7 hours at 185° C. to 190° C. Vacuum distillation gave 39 g of 2,6-difluoro-3-trifluoromethylbenzaldehyde having a boiling point of 49 to 51° C. at 10 mbar and a refractive index $n^{20}_D$ of 1.4492.

EXAMPLE 6

Preparation of a few starting materials of the formula (II)

450 ml of conc. sulphuric acid were initially placed in a stirred apparatus, and 195 g of a dichlorotrifluoromethylbenzal chloride or trichlorotrifluoromethylbenzal chloride were added dropwise at 45 to 50° C. Stirring was continued for 4 hours and the mixture was then poured onto ice. The organic phase was separated off and distilled in vacuo. Between 100 and 138 g of the corresponding dichlorotrifluoromethylbenzaldehyde or trichlorotrifluoromethylbenzaldehyde were produced.

The following were obtained in this way:
a) 2,6-dichloro-3-trifluoromethylbenzaldehyde (boiling point: 125–128° C./24 mbar, melting point: 48–50° C.),
b) 4,5-dichloro-2-trifluoromethylbenzaldehyde (boiling point: 106° C./20 mbar, $n^{20}_D$1.5165),
c) 2,3-dichloro-4-trifluoromethylbenzaldehyde (boiling point: 114–117° C./20 mbar),
d) 2,4-dichloro-5-trifluoromethylbenzaldehyde (boiling point: 105–107° C./14 mbar),
e) 2,6-dichloro-4-trifluoromethylbenzaldehyde (boiling point: 110–113° C./15 mbar),
f) 2,3,4-trichloro-5-trifluoromethylbenzaldehyde,
g) 2,4,6-trichloro-5-trifluoromethylbenzaldehyde,
h) 2,3,6-trichloro-4-trifluoromethylbenzaldehyde,
i) 2,3,6-trichloro-5-trifluoromethylbenzaldehyde,
j) 2,3,4-trichloro-6-trifluoromethylbenzaldehyde,
k) 3,4,5-trichloro-2-trifluoromethylbenzaldehyde,
l) 2,5-dichloro-4-trifluoromethylbenzaldehyde and
m) 2,3,5-trichloro-4-trifluoromethylbenzaldehyde.

EXAMPLE 7

2-Fluoro-3-trifluoromethylbenzaldehyde 109 g of potassium fluoride were initially taken together with 210 ml of tetramethylene sulphone and the mixture was incipiently distilled in vacuo to achieve dryness. 10 g of 18-crown-6 ether and 218 g of 2-chloro-3-trifluoromethylbenzaldehyde were then added and the mixture was heated at 190° C. for 5 hours with the exclusion of moisture (quantitative conversion according to GC). Vacuum distillation afforded 157 g of 2-fluoro-2-trifluoromethylbenzaldehyde (boiling point 60° C./20 mbar).

What is claimed is:

1. Nuclear-fluorinated trifluoromethylbenzaldehydes selected from the group comprising
2-trifluoromethyl-4,6-difluorobenzaldehyde,
2-trifluoromethyl-4-chloro-6-fluorobenzaldehyde,
2-trifluoromethyl-4-fluoro-6-chlorobenzaldehyde,
2-trifluoromethyl-4-fluoro-5-chlorobenzaldehyde,
2-trifluoromethyl-4,5-difluorobenzaldehyde,
3-trifluoromethyl-4,5-difluorobenzaldehyde,
3-trifluoromethyl-4-fluoro-5-chlorobenzaldehyde,
2,4-difluoro-b 3-trifluoromethylbenzaldehyde,
3-trifluoromethyl-4,6-difluorobenzaldehyde,
2-fluoro-4-trifluoromethyl-b 5-chlorobenzaldehyde,
2-fluoro-3-chloro-4-trifluoromethylbenzaldehyde,
2,4-difluoro-4-trifluoromethylbenzaldehyde,
2,6-difluoro-4-tribluoromethylbenzaldehyde,
2-chloro-4-trifluoromethyl-6-fluorobenzaldehyde,
3-chloro-4-trifluoromethyl-6-fluorobenzaldehyde,
2,6-difluoro-4-trifluoromethyl-5-chlorobenzaldehyde,
2,5,6-trifluoro-3-trifluoromethylbenzaldehyde,
2,6-difluoro-3-trifluoromethyl-5-chlorobenzaldehyde,
2,4,6-trifluoro-3-trifluoromethylbenzaldehyde,
2-trifluoromethyl-3-chloro-4,6-difluorobenzaldehyde and
2-trifluoromethyl-3,4,6-trifluorobenzaldehyde.

* * * * *

UNITED STATES PATENT AND TRADEMARK OFFICE
CERTIFICATE OF CORRECTION

PATENT NO. : 5,041,683

DATED : August 20, 1991

INVENTOR(S) : Marhold et al.

It is certified that error appears in the above-identified patent and that said Letters Patent is hereby corrected as shown below:

Col. 6, line 34   After " difluoro- " delete " b "

Col. 6, line 36   After " trifluoromethyl- " delete " b "

Col. 6, line 39   Delete " tribluoromethylbenzaldehyde " and substitute -- trifluoromethylbenzaldehyde --

Signed and Sealed this

Fourth Day of May, 1993

Attest:

MICHAEL K. KIRK

*Attesting Officer*   Acting Commissioner of Patents and Trademarks